US005492894A

United States Patent [19]

Bascom et al.

[11] Patent Number: 5,492,894
[45] Date of Patent: Feb. 20, 1996

[54] COMPOSITIONS FOR TREATING WRINKLES COMPRISING A PEPTIDE

[75] Inventors: Charles C. Bascom, Hamilton; Andrew W. Fulmer, Loveland, both of Ohio

[73] Assignee: The Procter & Gamble Company, Cincinnati, Ohio

[21] Appl. No.: 82,847

[22] Filed: Jun. 25, 1993

Related U.S. Application Data

[63] Continuation-in-part of Ser. No. 62,043, May 14, 1993, abandoned, which is a continuation-in-part of Ser. No. 673,381, Mar. 21, 1991, abandoned.

[51] Int. Cl.⁶ .......................... A61K 38/00; C07K 5/00; C07K 7/00; C07K 16/00
[52] U.S. Cl. .................. 514/18; 514/17; 530/300; 530/329; 530/330; 530/331
[58] Field of Search ........................ 514/12, 18, 17, 514/16, 15; 530/300, 324, 328, 329, 330, 331

[56] References Cited

U.S. PATENT DOCUMENTS

| | | | |
|---|---|---|---|
| 4,181,717 | 1/1980 | Kent, Jr. | 574/18 |
| 4,683,291 | 7/1987 | Zimmerman et al. | 530/324 |
| 4,785,079 | 11/1988 | Gospodarowicz et al. | 530/399 |
| 4,902,782 | 2/1990 | Gospodarowicz et al. | 530/399 |
| 4,943,562 | 7/1990 | Jolles et al. | 514/18 |
| 4,956,455 | 9/1990 | Esch et al. | 530/399 |
| 5,079,231 | 1/1992 | Brunetti et al. | 514/15 |

FOREIGN PATENT DOCUMENTS

| | | |
|---|---|---|
| 2000243 | 10/1988 | Canada . |
| 2000254 | 4/1990 | Canada . |
| 166612 | 1/1986 | European Pat. Off. . |
| 237966 | 9/1987 | European Pat. Off. . |
| 0246753 | 11/1987 | European Pat. Off. . |
| 275204 | 7/1988 | European Pat. Off. . |
| 281822 | 9/1988 | European Pat. Off. . |
| 288687 | 11/1988 | European Pat. Off. . |
| 0298723 | 1/1989 | European Pat. Off. . |
| 297262 | 1/1989 | European Pat. Off. . |
| 326907 | 8/1989 | European Pat. Off. . |
| 0339905 | 11/1989 | European Pat. Off. . |
| 0353565 | 2/1990 | European Pat. Off. . |
| 353565 | 7/1990 | European Pat. Off. . |
| 426074 | 5/1991 | European Pat. Off. . |
| 2533438 | 3/1984 | France . |
| 61-176599 | 1/1985 | Japan . |
| 2178207 | 7/1990 | Japan . |
| 83/02272 | 7/1983 | WIPO . |
| 87/01728 | 3/1987 | WIPO . |
| 92/15279 | 9/1992 | WIPO . |

OTHER PUBLICATIONS

Esch et al., "Primary Structure of Bovine Pituitary Basic Fibroblast Growth Factor (FGF) and Comparison with the Amino–terminal Sequence of Bovine Brain Acidic FGF", *Proc. of the Natl. Acad. Sci.*, vol. 82, pp. 6507–6511, Oct. 1985.

Abraham, J. A., A. Mergia, J. L. Whang, A. Tumolu, J. Friedman, K. A. Hjerrild, D. Gospodarowicz, & J. C. Fiddes, "Nucleotide Sequece of a Bovine Clone Encoding the Angiogenic Protein, Basic Fibroblast Growth Factor", *Science*, vol. 233, pp. 545–548 (1986).

Baird, A., N. Ueno, F. Esch, & N. Ling, "Distribution of Fibroblast Growth Factors (FGFs) in Tissues and Structure–function Studies with Synthetic Fragments of Basic FGF", *Journal of Cellular Physiology Supplement*, vol. 5, pp. 101–106 (1987).

Baird, A., D. Schubert, N. Ling, & R. Guillemin, "Receptor– and Heparin–binding Domains of Basic Fibroblast Growth Factor", *Proc. of the Natl. Acad. of Sci.*, vol. 85, pp. 2324–2328 (1988).

Maryash, L. I., V. A. Shibnev, & V. K. Burichenko, "Synthesis of the H2B Histone Fragment with the Amino Acid Sequence 30–39 and its Lys$^{31, 33}$ Analog", vol. 5, pp. 499–505 (1978).

Noszál, B., R. Kassai–Tánczos, J. Nyíri, O. Nyéki, & I. Schön, "Acid–base Properties of Thymopoietin–type Tri– and Tetrapeptides and their Derivatives", *Int. J. Peptide Protein Res.*, vol. 38, pp. 139–145 (1991).

*Primary Examiner*—Jill Warden
*Assistant Examiner*—A. M. Davenport
*Attorney, Agent, or Firm*—Brahm J. Corstanje; Richard A. Hake; David L. Suter

[57] ABSTRACT

The present invention relates to topical compositions comprising a peptide having the formula $$Q^a\text{-}(Xaa)_n\text{-}Q^c$$

wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino; n is an integer selected from the group consisting of 3, 4, 5 and 6; Xaa is independently any amino acid; and at least three of the amino acids are selected from the group consisting of arginine and lysine.

30 Claims, No Drawings

COMPOSITIONS FOR TREATING WRINKLES COMPRISING A PEPTIDE

This is a continuation-in-part of application Ser. No. 08/062,043, filed on May 14, 1993, and now abandoned, which is a continuation-in-part of application Ser. No. 07/673,381, filed on Mar. 21, 1991 and now abandoned.

TECHNICAL FIELD

The present invention relates to the field of anti-aging of skin. Specifically, the invention relates to novel compounds, compositions comprising such compounds and methods of using such compounds and compositions for regulating wrinkles in mammalian skin.

BACKGROUND OF THE INVENTION

Skin is subject to abuse by many extrinsic (environmental) factors as well as intrinsic (chronoaging) factors. A common extrinsic factor is exposure to ultraviolet radiation. Whether extrinsic or intrinsic, the abuse results in wrinkling of the skin. To many people, skin wrinkles are a reminder of the disappearance of youth. As a result, the elimination of wrinkles has become a booming business in youth-conscious societies. Treatments range from cosmetic creams and moistufizers to various forms of cosmetic surgery.

Chronoaging results in the thinning and general degradation of skin. As the skin naturally ages, there is a reduction in the cells and blood vessels that supply the skin. There is also a flattening of the dermal-epidermal junction which results in weaker mechanical resistance of this junction. As a consequence, older persons are more susceptive to blister formation in cases of mechanical trauma or disease processes. (See Oikarinen, (1990) "The Aging of Skin: Chronoaging Versus Photoaging", PHOTODERMATAL. PHOTOIMMUNOL. PHOTOMED. Vol. 7, pp. 3–4).

The tetrapeptide Arg-Ser-Arg-Lys, a preferred active of the present invention, is a basic fibroblast growth factor (hereinafter b-FGF) derived peptide corresponding to positions 107–110. European Patent Application 246 753, Baird and Ling, assigned to The Salk Institute for Biological Studies, published Nov. 25, 1987, discloses peptides derived from b-FGF, including the tetrapeptide Arg-Ser-Arg-Lys. The peptides are disclosed as being useful as FGF antagonists, which slow down or decrease cellular activity.

Baird, A., D. Schubert, N. Ling and R. Guillemin, (1988) "Receptor- and Heparin-binding Domains of Basic Fibroblast Growth Factor", PROCEDURES OF THE NATIONAL ACADEMY OF SCIENCES, Vol. 85, pp. 2324–2328, discloses b-FGF fragments whose amino acid sequences extend beyond positions 107–110 and act as potent antagonists in b-FGF present assays and as a slight agonist in b-FGF absent assays.

European Patent Application 339 905, Sheffield and Mezick, assigned to Ethicon Inc., published Nov. 2, 1989, discloses compositions comprising b-FGF or acidic FGF and a retinoid.

OBJECTS OF THE PRESENT INVENTION

It is an object of the present invention to provide novel peptides useful for regulating wrinkles in mammalian skin.

It is also an object of the present invention to provide compositions for topical application for regulating wrinkles in mammalian skin.

It is also an object of the present invention to provide methods of regulating wrinkles in mammalian skin which comprise treating the skin with safe and effective amounts of compositions for regulating wrinkles.

SUMMARY OF THE INVENTION

The present invention relates to compositions for regulating wrinkles in mammalian skin comprising a safe and effective amount of a peptide having the amino acid sequence:

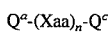

$$Q^a\text{-}(Xaa)_n\text{-}Q^c$$

wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino; n is an integer selected from the group consisting of 3, 4, 5 and 6; Xaa is independently any amino acid; and at least three of the Xaa are independently selected from the group consisting of arginine and lysine.

The present invention further relates to a method for regulating skin wrinkles in mammalian skin comprising treating the skin with a safe and effective amount of a composition of the present invention.

DETAILED DESCRIPTION OF THE INVENTION

As used herein, "anti-wrinkle agent" means a compound having Structure I, Structure II, or preferred embodiments thereof.

As used herein, "topical application" means directly laying on or spreading on outer skin.

As used herein, "cutaneous injection" means introduction of a substance beneath or within the skin by a hypodermic needle.

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio. Pharmaceutically-acceptable carriers must be of sufficiently high purity and sufficiently low toxicity to render them suitable for administration to the human or lower animal being treated.

As used herein, "cosmetically-acceptable" means that inert ingredients which the term describes are suitable for use in contact with the tissues of humans and lower animals without undue/unacceptable aesthetic effects, e.g., greasiness, color, odor, etc.

As used herein, "comprising" means that other steps and other ingredients which do not affect the end result can be added. This term encompasses the terms "consisting of" and "consisting essentially of".

As used herein, "regulating wrinkles" means preventing, retarding arresting and/or reversing the process of wrinkle formation in mammalian skin. Another manifestation often associated with regulating wrinkles is a smoother feel to the skin. In one embodiment of the invention, the anti-wrinkle agent regulates wrinkles. In another embodiment of the invention, the anti-wrinkle agent prevents the formation of wrinkles. In another embodiment of the invention, the anti-wrinkle agent retards the formation of wrinkles. In another embodiment of the invention, the anti-wrinkle agent arrests the formation of wrinkles. In another embodiment of the invention, the anti-wrinkle agent reverses the formation of wrinkles.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "alkyl" and "R" mean a hydrocarbon chain which may be straight, or branched; substituted (mono- or poly-) or unsubstituted, preferably unsubstituted; saturated or monounsaturated (i.e., one double or triple bond in the chain), or polyunsaturated (i.e., two or more double bonds in the chain, two or more triple bonds in the chain, or one or more double and one or more triple bonds in the chain).

As used herein, "aryl" and "Ar" mean an aromatic; substituted (mono- or poly-) or unsubstituted, preferably unsubstituted. Preferred aryls are phenyl, pyridyl, pyrmidyl and napthyl; more preferred is phenyl.

As used herein, "arylalkyl" means Ar—R—.

As used herein, "alkyloyl" means R—C(O)—.

As used herein, "aryloyl" means Ar—C(O)—.

As used herein, "arylalkyloyl" means Ar—R—C(O)—.

As used herein, "alkyloxoyl" means R—O—C(O)—.

As used herein, "aryloxoyl" means Ar—O—C(O)—.

As used herein, "arylalkyloxoyl" means Ar—R—O—C(O)—.

As used herein, "alkyloxy" means R—O—.

As used herein, "aryloxy" means Ar—O—.

As used herein, "arylalkyloxy" means Ar—R—O—.

As used herein, "alkylamino" means R—N(H)—.

As used herein, "dialkylamino" means $R_2N$—.

As used herein, "arylamino" means Ar—N(H)—.

As used herein, "diarylamino" means $(Ar)_2N$—.

As used herein, "(aryl)(alkyl)amino" means Ar—N(R)—.

As used herein, "arylalkylamino" means Ar—R—N(H)—.

As used herein, "diarylalkylamino" means $(Ar—R)_2N$—.

As used herein, "(alkyl)(arylalkyl) amino" means Ar—R—N(R)—.

As used herein, "(aryl)(arylalkyl)amino" means Ar—R—N(R)—.

All parts, percentages and ratios used herein are by weight unless otherwise specified.

Active Peptides

As used herein, "Structure I" means a peptide, or pharmaceutically-acceptable salt thereof, having the amino acid sequence:

wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino; n is an integer selected from the group consisting of 3, 4, 5 and 6; Xaa is independently any amino acid; and at least three of the Xaa are independently selected from the group consisting of arginine and lysine.

The amino acids making up the peptide may be in any combination of L- and D-configurations. In a preferred embodiment, all the amino acids are in the L-configuration.

As used herein, "amino acid" refers to any naturally or non-naturally occurring, L- or D- configuration, organic-acid having the structure

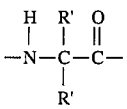

wherein each —R' is independently selected from the group consisting of hydrogen and an alkyl having from 1 to about 12 carbon atoms. Preferably at least one —R' of each amino acid is hydrogen. Preferably, the amino acid is naturally occurring.

As used herein, "naturally occurring amino acids" mean the following amino acids:

| Amino Acid | Three-letter Symbol |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

In one embodiment of the invention, the anti-wrinkle agent is a peptide having the amino acid sequence $Q^a$-Arg-Lys-Arg-$Q^c$, wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino. Preferably $Q^a$ is hydrogen and $Q^c$ is hydroxy, i.e., H-Arg-Lys-Arg-OH. Preferably $Q^a$ is $H_3C$—C(O)— and $Q^c$ is amino, i.e., $H_3C$—C(O)—Arg-Lys-Arg-$NH_2$.

In another embodiment of the invention, the anti-wrinkle agent is a peptide having the amino acid sequence $Q^a$-Arg-Gly-Arg-Lys-$Q^c$, wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino. Preferably $Q_a$ is hydrogen and $Q^c$ is hydroxy (SEQ ID NO: 1).

In another embodiment of the invention, the anti-wrinkle agent is a peptide having the amino acid sequence $Q^a$-Lys-Arg-Ser-Arg-$Q^c$, wherein $Q_a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino. Preferably $Q_a$ is hydrogen and $Q^c$ is hydroxy (SEQ ID NO: 2). Preferably, $Q^a$ is hydrogen and $Q^c$ is $NH_2$.

In another embodiment of the present invention, Structure I does not include the peptide Arg-Ser-Arg-Lys.

Arg-Ser-Arg-Lys Based Active Peptides

As used herein, "Structure II" means a peptide having the amino acid sequence:

$Q^a$-(Xaa)$_n$ Arg Ser Arg Lys (Xaa)$_n$ -$Q^c$ wherein each n is independently an integer selected from the group consisting of 0, 1, 2 and 3; each amino acid is protected or unprotected, each Xaa is independently any amino acid, $Q^a$ is selected from the group consisting of hydrogen and an amino terminus blocking group; and $Q^c$ is selected from the group consisting of hydrogen and a carboxy-terminus blocking group.

In the above peptide structure, each n is independently preferably 0, 1, 2 or 3, more preferably 0, 1 or 2, more preferably still 0 or 1, most preferably 0.

The amino acids making up the peptide may be any combination of L- and D-configurations. In a preferred embodiment, all the amino acids are in L-configuration.

In the above peptide structure, each amino acid is independently preferably unprotected.

In a preferred embodiment of the present invention, the peptide comprising the core sequence Arg-Ser-Arg-Lys (SEQ ID NO:3), illustrated as

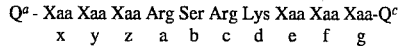

$Q^a$ - Xaa Xaa Xaa Arg Ser Arg Lys Xaa Xaa Xaa-$Q^c$
     x   y   z   a   b   c   d   e   f   g constitutes amino acid positions a through d, respectively, from amino terminus to carboxy terminus. The peptide may have from 0 to 3, preferably 0, amino acids independently bound through amide linkages usual for peptides to the amino terminus and/or the carboxy terminus. Preferably, the z and e position amino acids are hydrophobic, more preferably tyrosine. Preferably, the y and f position amino acids are hydrophilic, more preferably selected from the group consisting of serine and threonine; more preferably still the y position amino acid is threonine and the f position amino acid is serine. Preferably, the x and g position amino acids are hydrophilic; more preferably the x position amino acid is asparagine, and the g position amino acid is serine.

The naturally occurring hydrophobic amino acids are Ala, Ile, Leu, Met, Phe, Pro, Hyp, Trp, Tyr, and Val.

The naturally occurring hydrophilic amino acids are Arg, Asn, Asp, Asx, Cys, Gln, Glu, Gly, His, Lys, Hyl, Ser, and Thr.

Specific amino acid sequences encompassed by Structure II are exemplified in SEQ ID NO:3 through SEQ ID NO:38. More preferably, the peptide has an amino acid sequence selected from the group consisting of SEQ ID NO: 3, 4, 5, 6, 7, 8, 9, 10, 11, 12, 13, 14, 15, 16 and 17; more preferably still SEQ ID NO: 3, 6, 14, and 17, most preferably SEQ ID NO: 3.

The peptide may also be blocked or unblocked. As used herein, "blocked peptide" means that the amino-terminus and/or the carboxy-terminus of the peptide is bound to a terminus blocking group, i.e., one or both of $Q^a$ or $Q^c$ is not hydrogen. Preferably either $Q^a$ or $Q^c$ is hydrogen; more preferably both $Q^a$ and $Q^c$ are hydrogen.

The amino terminus of the peptide may comprise an amino-terminus blocking group. As used herein, "amino-terminus blocking group" means a fatty acid, free amine, acetamide or a terminal amino protecting group. Examples of terminal amino protecting groups can be found in THE PRACTICE OF PEPTIDE SYNTHESIS, pp. 9–31 (wherein they are referred to as amine protecting groups) (1984), incorporated herein by reference, and are further defined below. Preferably, the fatty acid is saturated or unsaturated, with a carbon chain length of from about 2 to about 30 carbons, preferably from about 8 to about 18 carbons, and may be linked to the amino terminus by an amide bond.

The carboxy terminus of the peptide may comprise a carboxy-terminus blocking group. As used herein, "carboxy-terminus blocking group" means a fatty amine, free acid, amide or a terminal carboxyl protecting group. Examples of terminus carboxyl protecting groups can be found in THE PRACTICE OF PEPTIDE SYNTHESIS, pp. 33–57 (wherein they are referred to as carboxyl protecting groups) (1984), incorporated herein by reference, and are further defined below. Preferably, the fatty amine is saturated or unsaturated, with a carbon chain length of from about 2 to about 30 carbons, preferably from about 8 to about 18 carbons, and may be linked to the carboxy terminus by an amide bond.

The peptide may also comprise a protecting group on one or more of the amino acid —R moieties in which case, the peptide is referred to as "protected". In the case of tyrosine, the protecting group is preferably selected from the group consisting of tetrahydropyranyl, tertbutyl, trityl, benzyl, carbobenzoxy (CBZ), 4-bromo-carbobenzoxy (4Br-CBZ) and 2,6-dichlorobenzyl. In the case aspartic acid or glutamic acid, the protecting group is preferably selected from the group consisting of benzyl, cyclohexyl, cycloheptal, 2,6-dichlorobenzyl, methyl and ethyl. In the case of cystfine, the protecting group is preferably selected from the group consisting of p-methoxybenzyl, p-methylbenzyl, acetamidomethyl, tfityl and benzyl. In the case of threonine or sefine, the protecting group is preferably selected from the group consisting of acetyl, benzoyl, tert-butyl, trityl, tetrahydropyranyl, benzyl, 2,6-dichlorobenzyl and CBZ. In the case of arginine, the protecting group is preferably selected from the group consisting of nitro, toluenesulfonyl (Tos), CBZ, acyladamantyloxycarbonyl and t-butyloxycarbonyl (BOC). In the case of lysine, the protecting group is preferably selected from the group consisting of 2-chlorobenzyloxycarbonyl, Tos, CBZ, t-amyloxycarbonyl and BOC. In the case of glutamine or asparagine, the protecting group is preferably xanthyl. In the case of histidine, the protecting group is preferably selected from the group consisting of Tos or dinitrophenyl. A more complete disclosure of such —R protecting groups can be found in The Practice of Peptide Synthesis, pp. 59–85 (1984), incorporated herein by reference. As used herein, "unprotected" means the peptide does not comprise any —R protecting groups.

Synthesis of Peptides

It may be preferable to synthesize the peptides of the present invention using recombinant DNA methods. Alternatively, it may be preferable to synthesize the peptides of the present invention using the well known chain elongation techniques such as solid-phase synthesis, as on a Merrifield resin or the like.

To synthesize a peptide using recombinant DNA, one typically synthesizes a double-stranded DNA chain which encodes the desired amino acid sequence. The degeneracy of the genetic code permits a wide variety of codon combinations to be used to form the DNA chain that encodes the product peptide. Certain particular codons are more efficient for peptide expression in certain types of organisms and the selection of codons preferably is made according to those codons which are most efficient for expression in the type of organism which is to serve as the host for the recombinant vector. However, any correct set of codons should encode the desired product, even if slightly less efficiently. Codon selection may also depend upon vector construction considerations, for example, it may be necessary to avoid creating a particular restriction site in the DNA chain if, subsequent to insertion of the synthetic DNA chain, the vector is to be manipulated using a restriction enzyme that cleaves at such a site. Also, it is necessary to avoid placing restriction sites in the DNA chain if the host organism which is to be transformed with the recombinant vector containing the DNA chain is known to produce a restriction enzyme that would cleave at such a site within the DNA chain.

In addition to the encoding sequences, the DNA chain that is synthesized may contain additional sequences, depending upon vector construction considerations. Typically, a DNA chain is synthesized with linkers at its ends to facilitate insertion into restriction sites within a cloning vector. The DNA chain may be constructed so as to encode the desired sequence as a portion of a fusion peptide and if so, it may contain terminal sequences that encode amino acid residue sequences that serve as proteolytic processing sites, whereby the desired peptide may be proteolytically cleaved from the remainder of the fusion peptide. The terminal portions of the synthetic DNA chain may also contain appropriate start and stop signals.

To assemble the desired DNA chain, oligonucleotides are constructed by conventional methods such as procedures described in T. Maniatis et al. COLD SPRING HARBOR LABORATORY MANUAL, Cold Spring Harbor, N.Y. (1982) (hereinafter CSH). Sense and antisense oligonucleotide chains up to about 70 nucleotide residues long are synthesized preferably on automated synthesizers such as the Applied Biosystems in model 380B DNA synthesizer. The oligonucleotide chains are constructed so that the sense and antisense oligonucleotides associate with each other through hydrogen bonding between complementary base pairs and thereby form double stranded chains. These oligonucleotides are then ligated to the vector.

The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E. coli*, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delargo sequence, and the encoding sequence is placed in correct reading frame with the ATG start codon. The cloning vector also provides a 3' non-translated region and a transcription termination site. A translation termination site could be provided by either the synthetic DNA or the cloning vector. For insertion into a eukaryotic cell, such as a yeast cell or a cell line obtained from a higher animal, the encoding oligonucleotide sequence is appropriately spaced from a capping site and in correct reading frame with an ATG start signal. The cloning vector also provides a 3' non-translated region and a polyadenylation site. A translation termination site could be provided by either the synthetic DNA or the vector.

Derivatives of prokaryotic vectors, such as pBR322, pMB9, Col El, pCRI, RP4 and lambda-phage, are available for inserting a DNA chain of the length necessary to encode peptides of interest with substantial assurance of at least some expression of the encoded peptide. Typically, such vectors are constructed or modified to have a unique restriction site(s) appropriately positioned relative to a promoter, such as the lac promoter. The DNA chain may be inserted with appropriate linkers into such a restriction site, with substantial assurance of production of peptide in a prokaryotic cell line transformed with the recombinant vector. To assure the proper reading frame, linkers of various lengths may be provided at the ends of the peptide-encoding sequence. Cassettes, which include sequences, such as the 5' region of the lac Z gene (including the operator, promoter, transcription start site, Shine Delgarno sequence and translation initiation signal), the regulatory region from the tryptophan gene (trp operator, promoter, ribosome binding site and translation initiator) and a fusion gene containing these two promoters, called the trp-lac or commonly called the Tac promoter, are available into which a synthetic DNA chain may be conveniently inserted.

Similarly, eukaryotic transformation vectors, such as the cloned bovine papilloma virus genome, the cloned genomes of the murine retroviruses, and eukaryotic cassettes, such as the pSV-2 gpt system (described by Mulligan and Berg, NATURE, Vol. 277, pp. 108–114, 1979), the Okayama-Berg cloning system (MOL. CELL BIOL., Vol. 2, pp. 161–170, 1982) and the expression cloning vector recently described by Genetics Institute (SCIENCE, Vol. 228, pp. 810–815, 1985). These provide substantial assurance of at least some expression of the peptide in the transformed eukaryotic cell line.

Another way to produce desired peptides is to produce the peptide initially as a segment of a gene-encoded fusion peptide. In such case, the DNA chain is constructed so that the expressed peptide has enzymatic processing sites flanking the peptide sequence or, more commonly, processing site at one side of the desired peptide. A peptide-encoding DNA chain may be inserted for example, into the beta-galactosidase gene for insertion into *E. coli,* in which case, the expressed fusion peptide is subsequently cleaved with appropriate proteolytic enzymes to release the peptide from beta-galactosidase peptide sequences.

Alternatively, the peptides can be synthesized by suitable chain elongation or coupling-type methods, such as by exclusively solid-phase techniques, by partial solid-phase techniques, by fragment condensation or by classical solution couplings. The techniques of exclusively solid-phase synthesis are set forth in the textbook "Solid-Phase Peptide Synthesis" Stewart & Young, Pierce Chemical Company, Rockford, Ill., 1984 and are exemplified by the disclosure of U.S. Pat. No. 4,105,603, issued Aug. 8, 1978, incorporated herein by reference. The fragment condensation method of synthesis is exemplified in U.S. Pat. No. 3,972,859 issued Aug. 3, 1976, incorporated herein by reference. Other available syntheses are exemplified by U.S. Pat. No. 3,842,067, issued Oct. 15, 1974 and U.S. Pat. No. 3,862,925 issued Jan. 28, 1975, both incorporated herein by reference.

Common to coupling-type syntheses is the protection of the labile side chain groups of the various amino acid moieties with suitable protecting groups which will prevent a chemical reaction from occurring at that site until the group is ultimately removed. Usually also common is the protection of an alpha-amino group by an amino-terminus blocking group on an amino acid or a fragment while that entity reacts at the carboxyl group, followed by the selective removal of the amino-terminus blocking group to allow subsequent reaction to take place at that location. Accordingly, it is common that, as a step in the synthesis, an intermediate compound is produced which includes each of the amino acid residues located in its desired sequence in the peptide chain with side-chain protecting groups or terminus blocking group linked to the appropriate residues.

With regard to the Arg-Ser-Arg-Lys based peptides, such an intermediate may have the formula:

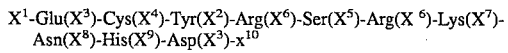
$X^1$-Glu($X^3$)-Cys($X^4$)-Tyr($X^2$)-Arg($X^6$)-Ser($X^5$)-Arg($X^6$)-Lys($X^7$)-Asn($X^8$)-His($X^9$)-Asp($X^3$)-$x^{10}$ In these formulae: $X^1$ is either hydrogen or an aminoterminus blocking group. The amino-terminus blocking groups contemplated by $X^1$ are those known to be useful in the art of step-wise synthesis of polypeptides. Among the classes of amino-terminus blocking groups covered by $X^1$ are (1) acyl-type protecting groups, such as formyl, trifluoroacetyl, phthalyl, toluenesulfonyl (Tos), benzensulfonyl, nitrophenylsulfenyl, tritylsulfenyl, o-nitrophenoxyacetyl, chloroacetyl, acetyl, and y-chlorobutyryl; (2) aromatic urethantype protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxy carbonyl, isopropyloxycarbonyl, ethoxycarbonyl, allyloxcarbonyl; (4) cycloalkyl urethan-type protecting groups, such as cyclopentyl oxcarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl; (7) trilakylsilane groups, such as trimethyl silane. The preferred amino-terminus blocking group is BOC.

$X^2$ is a protecting group for the phenolic hydroxyl group of Tyr selected from the group consisting of tetrahydropyranyl, tert-butyl, trityl, Bzl, CBZ, 4Br-CBZ and 2,6-dichlorobenzyl. The preferred protecting group is 2,6-dichlorobenzyl, X2 can be hydrogen which means that there is no protecting group on the hydroxyl group.

$X^3$ is hydrogen or an ester-forming protecting group for the carboxyl group of Asp or Glu and is selected from the group consisting of Bzl, cyclohexyl, cycloheptal, 2,6-dichlorobenzyl, methyl and ethyl.

$X^4$ is a protecting group for Cys selected from the group consisting of p-methoxybenzyl(MeOBzl), p-methoxylbenzyl(MeOBzl), p-methylbenzyl, acetamidomethyl, trityl and Bzl. The most preferred protecting group is p-methoxybenzyl. $X^4$ can also be hydrogen, meaning that there is no protecting group on the sulfhydryl.

$X^5$ is a protecting group for the hydroxyl group of Thr and Ser and is selected from the group consisting of acetyl, benzoyl, tert-butyl, trityl tetrahydropyranyl, Bzl, 2,6-dichlorobenzyl and CBZ. The preferred protecting group is Bzl. X5 can be hydrogen, which means there is no protecting group on the hydroxyl group.

$X^6$ is a protecting group for the guanido group of Arg selected from the group consisting of nitro, Tos, CBZ, adamantyloxycarbonyl, and BOC, or is hydrogen.

$X^7$ is hydrogen or a protecting group for the side chain amino substituent of Lys. Illustrative of suitable side chain amino protecting groups are 2-chlorobenzyloxycarbonyl(2-Cl-Z), Tos, CBZ, 1-amyloxycarbonyl and BOC.

The selection of a side chain amino protecting group is not critical except that it must be one which is not removed during deprotection of the a-amino groups during the synthesis. Hence, the a-amino protecting group and the side chain amino protecting group cannot be the same.

$X^8$ is a protecting group for the side chain amido group of Gln and/or Asn and is preferably xanthyl (Xan). Optionally X8 can be hydrogen.

$X^9$ is a protecting group for the imidazole nitrogen of His such as Tos or dinitrophenyl or may be hydrogen.

$X^{10}$ is either hydrogen or a carboxy-terminus blocking group selected from the class consisting of $OCH_2$, esters, amides, hydrazides, $—O—CH_2—$ resin support and $—NH$-resin support, with the groups other than OH and amides being broadly considered as carboxy-terminus blocking groups.

In the formula for the intermediate, at least one of $X^1$, $X^2$, $X^3$, $X^4$, $X^5$, $X^6$, $X^7$, $X^8$, $X^9$ and $X^{10}$ is an —R protecting group/terminal amino protecting group/terminal carboxyl protecting group.

In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions, and (c) the side chain protecting group should be removable, upon the completion of the synthesis containing the desired amino acid sequence, under reaction conditions that will not alter the peptide chain.

The peptides are preferably prepared using solid phase synthesis, such as that described by Merrifield, J. AM. CHEM. SOC., Vol. 85, pp. 2149 (1963), although other equivalent chemical syntheses known in the art can also be used as previously mentioned. Solid-phase synthesis is commenced from the C-terminal end of the peptide by coupling a protected a-amino acid to a suitable resin. Such a starting material can be prepared by attaching a-amino-protected Val by an ester linkage to a chloromethylated resin or a hydroxymethyl resin, or by an amide bond to a butylated hydroxy anisole (BHA) resin or MBHA resin. The preparation of the hydroxymethyl resin is described by Bodansky et al., CHEM. IND. (London) Vol. 38, pp. 1597–98 (1966). Chloromethylated resins are commercially available from Bio Rad Laboratories, Richmond, California and from Lab. Systems, Inc. The preparation of such a resin is described by Stewart et al, "Solid Phase Peptide Synthesis" (Freeman & Co., San Francisco 1969), Chapter 1, pp. 1–6. BHA and MBHA resin supports are commercially available and are generally used only when the desired polypeptide being synthesized has an a-carboxamide at the C-terminal.

For example, a peptide of the first family can be prepared by coupling Lys, protected by BOC, to a chloromethylated resin according to the procedure of Monahan and Gilon, BIOPOLYMER, Vol. 12, pp. 2513–19, (1973) when, for example, it is desired to synthesize such a peptide with free carboxy terminus. Following the coupling of BOC-Lys, the a-amino protecting group is removed, as by using trifluoroacetic acid (TFA) in methylene chloride, TFA alone or HCl in dioxane. The deprotection is carried out at a temperature between about 0° C. and room temperature. Other standard cleaving reagents and conditions for removal of specific a-amino protecting groups may be used as described in Schroder & Lubke, "The Peptides", pp. 72–75 (Academic Press 1965).

After removal of the a-amino protecting group of Val, the remaining a- amino-and side chain-protected amino acids are coupled stepwise in the desired order to obtain an intermediate compound as defined hereinbefore. As an alternative to adding each amino acid separately in the synthesis, some of them may be coupled to one another prior to their addition to the solid phase reactor. The selection of an appropriate coupling reagent is within the skill of the art; particularly suitable as a coupling reagent is N,N-dicyclohexylcarbodiimide (DCCI).

Activating reagents used in solid phase synthesis of the peptides are well known in the peptide synthesis art. Examples of suitable activating reagents are (1) carbodiimides, such as N,N-diisopropylcarbodiimide, N,N-dicyclohexylcarbodiimide (DCCI); (2) cyanamides such as N,N-dibenzylcyanamide; (3) keteimines; (4) isoxazolium salts, such as N-ethyl-5-phenyl isoxazolium-3-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N-carbonyl diimidazole, N,N-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) reagents which form an active ester with the carboxyl moiety of the amino acid, such as nitrogen-containing heterocyclic compounds having a hydroxy group on one ring nitrogen, e.g., N-hydroxyphthalimide, N-hydroxysuccinimide and 1-hydroxybenzotriazole (HOBT). Other activating reagents and their use in peptide coupling are described by Schroder & Lubke supra, in Chapter III and by Kapoor, J. PHAR. SCI., Vol. 59, pp. 1–27 (1970).

Each protected amino acid or amino acid sequence is introduced into the solid phase reactor in about a twofold or more excess, and the coupling may be carried out in a medium of dimethylformamide (DMF)—$CH_2C_{12}$ (1:1) or in DMF or $CH_2Cl_2$ alone. In cases where incomplete coupling occurs, the coupling procedure is repeated before removal of the a-amino protecting group prior to the coupling of the next amino acid. If performed manually, the success of the coupling reaction at each stage of the synthesis is monitored by the ninhydrin reaction, as described by E. Kaiser et al., ANAL. BIOCHEM., Vol. 34, pp. 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$, $X^8$ and $X^9$ and the a-amino protecting group $X^1$ to obtain the peptide.

As an alternative route, the intermediate peptide may be separated from the resin support by alcoholysis after which the recovered C-terminal alkyl ester is converted to the acid by hydrolysis. Any side chain protecting groups may then be cleaved as previously described or by other known procedures, such as catalytic reduction (e.g., Pd on $BaSO_4$). When using hydrogen fluoride for cleaving, anisole and methylethyl sulfide are included in the reaction vessel for scavenging.

EXAMPLE 1

Synthesis of H-Arg-Lys-Arg-OH

The peptide H-Arg-Lys-Arg-OH is synthesized according to the Merrifield solid phase method (*Journal of the American Chemical Society*, (1983), Vol. 85, p. 2149), using a resin consiting of a polystyrene-divinylbenzene copolymer functionalized with chlormethyl groups (the "Merrifield resin"). The α-amino acids are protected by t-butyloxycarbonyl (Boc). The side chain protecting group for the guanidino group of arginine is N-p-toluenesulfonyl (Tos) and for lysine the side chain is protected with 2-chlorobenzyloxycarbonyl (2-Cl-Z).

The C-terminal arginine is attached to 1% crosslinked chloromethylated polystryene resin (about 0.5–0.8 meq Cl/gram resin). The formation of the benzylester bond is accomplished by incubating the Bos-Arg(Tos) with the resin in dimethylformamide (DMF) containing potassium fluoride. This solution is then heated overnight at 80° C. The resin is then washed, and the Boc protecting group is removed by treatment with 50% trifluoroacetic acid (TFA) in methylene chloride. The resin is washed again, to remove the TFA, and is subsequently neutralized by successive washes with 10% triethylamine in mehtylene chloride. Following successive washes in methanol and methylene chloride the resin is ready for the next coupling reaction.

For all coupling reactions a 3–4 fold excess of Boc-amino acid, either BocLys( 2-Cl-Z) or Boc-Arg(Tos), in methylene chloride is mixed with the resin in the presence of an equal amount of the coupling reagent, dicyclohexylcarbodiimide (DCC). Arginine is added to the coupling reaction in 10% DMF in methylene chloride. This mixture is then incubated at room temperature for 1–2 hours. Following this coupling reaction, the resin is subjected to the same cycle of deprotection, neutralization and coupling previously stated to complete the synthesis fo the tripeptide.

Detachment of the tripeptide from the resin, along with deprotection of the side chains, is accomplished by treatment wiht anhydrous hydrogen fiouride (HF) for 60 minutes at 0° C. in the presence of anisole ((30%) w/v). FIF is removed by a dry nitrogen gas flow. Dry ether is then added and the mixture is incubated for 1 hour at 4° C. to remove anisole. The crude mixture of peptide is then extracted with 1% acetic acid and lyophilized.

The crude peptide is resuspended in water, filtered, and then loaded onto a C18 column and eluted with 0.1% TFA in acetonitrile. Fractions which display a high degree of purity (>98%) are collected and lyophilized. The peptide is again resuspended in water. The peptide is then applied to a Bio Rex 70 ion exchange column in the acetate form, where it is shown to have a similar degree of purity when analyzed.

EXAMPLE 2

Synthesis of H-Arg-Gly-Arg-Lys-OH (SEQ ID NO: 1)

The peptide H-Arg-Gly-Arg-Lys-OH (SEQ ID NO: 1) is synthesized according to the Merrifield solid phase method as well, using a resin consisting of a polystyrene-divinylbenzene copolymer functionalized with chloromethyl groups (the "Merrifield resin"). The α-amino acids are protected by t-butyloxycarbonyl (Boc). The side chain protecting group for the guanidino group of arginine is N-p-toluenesulfonyl (Tos) and for lysine the side chain is protected with 2-chlorobenzyloxycarbonyl (2-Cl-Z).

The C-terminal lysine is attached to 1% crosslinked chloromethylated polystyrene resin (about 0.5–0.8 meq Cl/gram resin). The formation of the benzylester bond is accomplished by incubating the Boc-Lys(2-Cl-Z) with the resin in dimethylformamide (DMF) containing potassium fluoride. This solution is then heated overnight at 80° C. The resin is then washed, and the Boc protecting group is removed by treatment with 50% trifluoracetic acid (TFA) in methylene chloride. The resin is washed again, to remove the TFA, and is subsequently neutralized by successive washes with 10% triethylamine in methylene chloride. Following successive washes in methanol and methylene chloride the resin is ready for the next coupling reaction.

For all coupling reactions a 3–4 fold excess of Boc-amino acid (either Boc-Gly or Boc-Arg(Tos)) in methylene chloride is mixed with the resin in the presence of an equal amount of the coupling reagent, dicyclohexylcarbodiimide (DCC). Arginine, however, is added to the coupling reaction in 10% DMF in methylene chloride. This mixture is then incubated at room temperature for 1–2 hours. Following this coupling reaction, the resin is subjected to the same cycle of deprotection, neutralization and coupling previously recorded to complete the synthesis of the peptide.

Detachment of the peptide from the resin, along with deprotection of the side chains, is accomplished by treatment with anhydrous hydrogen fluoride (HF) for 60 minutes at 0° C. in the presence of anisole (30% w/v). HF is removed by a dry nitrogen gas flow. Dry ether is then added and the mixture is incubated for 1 hour at 4° C. to remove anisole. The crude mixture of peptide is then extracted with 1% acetic acid and lyophilized.

The crude peptide is resuspended in water, filtered, and then loaded onto a C18 column and purified.

EXAMPLE 3

Synthesis of H-Lys-Arg-Ser-Arg-NH$_2$

The C-terminal blocked peptide, H-Lys-Arg-Ser-Arg-NH$_2$, is synthesized using an methyl-benzylhydramine (MBHA) resin. The α-amino acids are protected by t-butyloxycarbonyl (Boc). The side chain protecting group for the guanidino group of arginine is N-p-toluenesulfonyl (Tox), for lysine the side chain is protected with 2-chlorobenzyloxycarbonyl (2-Cl-Z) and serine is blocked with the benzyl (Bzl) group.

The C-terminal arginine is attached to the MBHA resin using standard coupling techniques. Initially, however, the MBHA resin is neutralized by successive washes in 10% triethylamine in methylene chloride. The resin is then washed in methanol and methylene chloride in preparation for the first coupling reaction. A 3–4 fold excess of the C-terminal Boc-Arg(Tos), in 10% DMF in methylene chloride, is then coupled to the resin in the presence of the coupling reagent, dicyclohexylcarbodiimide (DCC). The resin is then washed, and the Boc protecting group is removed by treatment with 50% trifluoroacetic acid (TFA) in methylene chloride. The resin is washed again, to remove the TFA, and is subsequently neutralized by successive washes with 10% triethylamine in methylene chloride. Following successive washes in methanol and methylene chloride the resin is ready for the next coupling reaction.

For all subsequent coupling reactions a 3–4 fold excess of Boc-amino acid (here, either Boc-Ser(Bzl), Boc-Arg(Toc), or Boc-Lys(2-Cl-Z) in methylene chloride is mixed with the resin in the presence of an equal amount of the coupling reagent, dicyclohexylcarbodiimide (DCC). Again, arginine is added to the coupling reaction in 10% DMF in methylene chloride. This mixture is then incubated at room temperature for 1–2 hours. Following the coupling reaction, the resin is subjected to the same cycle of deprotection, neutralization and coupling previously recorded to complete the synthesis of the peptide.

Detachment of the peptide from the resin, along with deprotection of the side chains, is accomplished by treatment with anhydrous hydrogen fluoride (HF) for 60 minutes at 0° C. in the presence of anisole (30% w/v). HF is removed by a dry nitrogen gas flow. Dry ether is then added and the mixture is incubated for 1 hour at 4° C. to remove anisole. The crude mixture of peptide is then extracted with 1% acetic acid and lyophilized.

The crude peptide is resuspended in water, filtered, and then loaded onto a C18 column and purified.

Pharmaceutical Compositions

The compositions of the present invention comprise a solid, semi-solid or liquid cosmetically and/or physiologically acceptable carrier to enable the anti-wrinkle agent to be delivered to the desired target at an appropriate concentration. The carrier can itself be inert or it can possess physiological or pharmaceutical benefits of its own. The nature of the carrier will be dictated by the method chosen for administration of the composition. A safe and effective amount of carrier is preferably from about 50% to about 99.9999%, more preferably from about 90% to about 99.9% of the composition. Variations in formulation of these carriers will result in a wide variety of products which fall within the scope of the present invention. The method of administration of the anti-wrinkle agent composition may range from internal methods such as injection to external topical methods.

A preferred method of administration of the anti-wrinkle agent is by cutaneous injection. The carrier for facillitation of such administration would preferably comprise water or a saline solution, preferably an isotonic saline solution.

A more preferred method of administration of the anti-wrinkle agent is by topical application. The topical pharmaceutical compositions of the present invention may be made into a wide variety of product types. These include, but are not limited to lotions, creams, beach oils, gels, sticks, sprays, ointments, pastes, mousses and cosmetics. These product types may comprise several types of carrier systems including, but not limited to, solutions, emulsions, gels and solids.

The topical pharmaceutical compositions of the present invention formulated as solutions typically include a pharmaceutically-acceptable aqueous or organic solvent. The terms "pharmaceutically-acceptable aqueous solvent" and "pharma ceutically-acceptable organic solvent" refer to a solvent which is capable of having dissolved therein the anti-wrinkle agent, and possesses acceptable safety properties (e.g., irritation and sensitization characteristics). Examples of suitable organic solvents include: propylene glycol, polyethylene glycol (degree of polymerization 200–600), polypropylene glycol (degree of polymerization 425– 2025), glycerol, 1,2,4-butanetriol, sorbitol esters, 1,2, 6-hexanetriol, ethanol, isopropanol, butanediol, and mixtures thereof. These solutions contain from about 0.001% to about 20%, more preferably from about 0.1% to about 10% of the anti-wrinkle agent, and from about 80% to about 99.999%, more preferably from about 90% to about 99.9% of an acceptable aqueous or organic solvent.

If the topical pharmaceutical compositions of the present invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagafin, Cosmetics Science and Technology, 2nd Edition, Vol. 2, pp. 443–465 (1972).

Topical pharmaceutical compositions of the present invention further comprise from about 2% to about 50% of a topical pharmaceutically-acceptable emollient. As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials. Examples of classes of useful emollients include the following:

1. Hydrocarbon oils and waxes. Examples include mineral oil, petrolatum, paraffin, ceresin, ozokerite, microcrystalline wax, polyethylene, and perhydrosqualene.

2. Silicone oil, such as dimethyl polysiloxanes, methylphenyl polysiloxanes, water-soluble and alcohol-soluble silicone glycol copolymers.

3. Triglyceride esters, for example vegetable and animal fats and oils. Examples include castor oil, safflower oil, cotton seed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl mono-stearate.

6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, dissohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples include oleyl myristate, oleyl stearate, and oleyl oleate.

8. Fatty acids having 10 to 20 carbon atoms. Suitable examples include pelargonic, laurie, myristic, palmitic, stearic, isostearic, hydroxystearic, oleic, linoleic, ricinoleic, arachidic, behenic, and erucic acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.

10. Fatty alcohol ethers. Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.

11. Ether-esters such as fatty acid esters of ethoxylated fatty alcohols.

12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols-esters, hydrogenolysis of lanolin, ethoxylated hydro genated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropyl sorbitol, polyethylene glycols 200– 6000, methoxy polyethylene glycols 350, 550, 750, 2000 and 5000, poly[ethylene oxide]homopolymers (100,000–5,000,000), polyalkylene glycols and derivatives, hexylene glycol (2-methyl-2,4-pentanediol), 1,3butylene glycol, 1,2,6-hexanetriol, ethohexadiol USP (2-ethyll, 3-hexanediol), C15–C18 vicinal glycol, and polyoxypropylene derivatives of trimethylolpropane are examples of this case of materials.

14. Polydydric alcohol esters. Ethylene glycol mono- and di-fatty acid esters, diethylene glycol mono- and di-fatty acid esters, polyethylene glycol (200– 6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxy lated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

15. Wax esters such as beeswax, spermaceti, myristyl myristate, stearyl stearate.

16. Beeswax derivatives, e.g., polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. hospholipids, such as lecithin and derivatives.

19. Sterols. Cholesterol and cholesterol fatty acid esters are examples thereof.

20. Amides such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives disclosed in U.S. Pat. No. 4,976,953, Orr and Sabatelli, issued Dec. 11, 1990. Preferably any of the compositions of the present invention comprises from about 1% to about 10% by weight of this propoxylated glycerol derivative. A lotion can be made from a solution carrier system.

Lotions typically comprise from about 0.001% to about 20%, preferably from about 0.1% to about 10%, of the anti-wrinkle agent; from about 1% to about 20%, preferably from about 5% to about 10%, of an emol lient; and from about 50% to about 90%, preferably from about 60% to about 80%, water.

Another type of product that may be formulated from a solution carrier system is a cream. A cream of the present invention would comprise from about 0.001% to about 20%, preferably from about 0.1% to about 10%, of the anti-wrinkle agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydro carbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. Examples of suitable thickening agents include: cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonitc), and carboxyvinyl polymers (CARBOPOLS™—sold by B. F. Goodrich Company, such polymers are described in detail in U.S. Pat. No. 2,798,053, Brown, issued Jul. 2, 1975, incorporated herein by reference). A more complete disclosure of thickening agents useful herein can be found in Segarin, Cosmetics, Science and Technology, 2nd Edition, Vol. 1, pp. 72–73 (1972), incorporated herein by reference.

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Diekert et al.; U.S. Pat. No. 4,421,769, issued Dec. 20, 1983, Dixon et al.; and MCCUTCHEON'S DETERGENTS AND EMULSIFIERS, North American Edition, pages 317–324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 0.001% to about 20%, preferably from about 0.01% to about 10%, of the anti-wrinkle agent; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.001% to about 20%, preferably from about 0.01% to about 10%, of the anti-wrinkle agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well known in the cosmetic an and are useful in the present invention. Multiphase emulsion compositions, such as the water-in-oil-inwater type, as disclosed in U.S. Pat. No. 4,254,105, Fakuda et al., issued Mar. 3, 1981, incorporated herein by reference, are also useful in the present invention. In general, such single or multiphase emulsions contain water, emollients and emulsifiers as essential ingredients.

Triple emulsion carrier systems comprising an oil-in-water in-silicone fluid emulsion composition as disclosed in U.S. Pat. No. 4,960,764, Figueroa, et al., issued Oct. 2, 1990, incorporated herein by reference, are also useful in the present invention. This triple emulsion carrier system can be combined with from about 0.001% to about 20%, preferably from about 0.01% to about 10%, of the anti-wrinkle agent to yield the topical pharmaceutical composition of the present invention.

Another emulsion carrier system useful in the topical pharmaceutical compositions of the present invention is a micro-emulsion carrier system. Such a system preferably comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 0.01% to about 10% of the anti-wrinkle agent.

If the topical pharmaceutical compositions of the present invention are formulated as a gel or a cosmetic stick, a suitable amount of a thickening agent, as disclosed supra, is added to a cream or lotion formulation.

The topical pharmaceutical compositions of the present invention may also be formulated as makeup products such as foundations. Foundations are solution or lotion-based with appropriate amounts of thickeners, pigments and fragrance.

The topical pharmaceutical compositions of the present invention may contain, in addition to the aforementioned components, a wide variety of additional oil-soluble materials and/or water-soluble materials conventionally used in topical compositions, at their an-established levels.

Various water-soluble materials may also be present in the compositions of this invention. These include humectants, such as glycerol, sorbitol, propylene glycol, alkoxylated glucose and hexanetriol, ethyl cellulose, polyvinyl alcohol, carboxymethyl cellulose, vegetable gums and clays such as VEEGUM™ (magnesium aluminum silicate, R. T. Vanderbilt, Inc.); proteins and poly peptides, preservatives such as the methyl, ethyl, propyl and butyl esters of hydroxybenzoic acid (Parabens - Mallinckrodt Chemical Corporation), EDTA, methylisothiazolinone and imidazolidinyl ureas (Germall 115 - Sutton Laboratories); and an alkaline agent such as sodium hydroxide or potassium hydroxide to neutralize, if desired, part of the fatty acids or thickener which may be present. In addition, the topical compositions herein can contain conventional cosmetic adjuvants, such as dyes, opacifiers (e.g., titanium dioxide), pigments and perfumes.

The topical pharmaceutical compositions of the present invention may also include a safe and effective amount of a penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published Jan. 13, 1982.

Other conventional skin care product additives may also be included in the compositions of the present invention. For example, collagen, hyaluronic acid, elastin, hydrolysates, prim rose oil, jojoba oil, epidermal growth factor, soybean saponins, mucopolysaccharides, and mixtures thereof may be used.

Various vitamins may also be included in the compositions of the present invention. For example, Vitamin A, and derivatives thereof, Vitamin $B_2$, biotin, pantothenic, Vitamin D, and mixtures thereof may be used.

Cleaning Compositions

The skin cleaning compositions of the present invention comprise, in addition to the anti-wrinkle agent, a cosmeticallyacceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the anti-wrinkle agent in a manner such that there is no interaction which would substantially reduce the efficacy of the composition for regulating wrinkles in mammalian skin.

The skin cleaning compositions of the present invention contain from about 0.001% to about 20%, preferably from about 0.01% to about 10%, of the anti-wrinkle agent and from about 1% to about 90%, preferably from about 5% to about 10%, of a cosmetically-acceptable suffactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions of the present invention are selected from anionic, nonionic, zwitterionic, amphoteric and ampholytic surfactants, as well as mixtures of these surfactants. Such surfactants are wellknown to those skilled in the detergency art.

The cleaning compositions of the present invention can optionally contain, at their art-established levels, materials which are conventionally used in skin cleansing compositions.

Combination Actives

A. Sunscreens and Sunblocks

Optimum regulation of skin wrinkling resulting from exposure to U.V. light can be obtained by using a combination of the anti-wrinkle agent of the present invention together with sunscreens or sunblocks. Useful sunblocks include, for example, zinc oxide and titanium dioxide.

Photodamage is a predominant cause of skin wrinkling. Thus, for purposes of wrinkle prevention, the combination of the anti-wrinkle agent with a UVA and/or UVB sunscreen would be most desirable. The inclusion of sunscreens in compositions of the present invention will provide immediate protection against acute UV damage. Thus, the sunscreen will prevent further wrinkle formation caused by UV radiation, while the anti-wrinkle agent regulates existing wrinkles and skin atrophy.

A wide variety of conventional sunscreening agents are suitable for use in combination with the anti-wrinkle agent. Segatin, et al., at Chapter VIII, pages 189 et seq., of Cosmetics Science and Technology, disclose numerous suitable agents. Specific suitable sunscreening agents include, for example: p-aminobenzoic acid, its salts and its derivatives (ethyl, iso butyl, glyceryl esters); p-dimethylaminobenzoic acid); anthrani lates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipro pyleneglycol esters); cinnamic acid derivatives (methyl and benzyl esters, α-phenyl cinnamonitrile; butyl cinnamoyl pyruvate); Dihydroxycinnamic acid derivatives (umbelliferone, methyl umbelliferone, methylaceto-umbelliferone); trihydroxycinnamic acid derivatives (esculetin, methylesculetin, daphnetin, and the glucosides, esculin and daphnin); hydrocarbons (diphenylbuta diene, stilbene); dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3bromoindazole, phenyl benzoxazole, methyl naphthoxazole, various aryl benzothiazoles); Quinine salts (bisulfate, sulfate, chloride, oleate, and tannate); Quinoline derivatives (8-hydroxy quinoline salts, 2-phenylquinoline); Hydroxy- or methoxy-sub stituted benzophenones; Uric and vilouric acids; Tannic acid and its derivatives (e.g., hexaethylether); (Butyl carbotol) (6propyl piperonyl) ether; Hydroquinone; Benzophenones (Oxybenzene, Sulisobenzone, Dioxybenzone, Benzoresorcinol, 2,2', 4,4'Tetrahydroxy-benzophenone, 2,2'-Dihydroxy-4,4'-dimethoxybenzophenone, Octabenzone; 4-Isopropyldibenzoyl-methane; Butylmethoxy dibenzoyl-methane; Etocrylene; and 4-isopropyl-diben-zoylmethane. Of these, 2-ethylhexyl-p-methoxycinnamate, 4,4'-t-butyl methoxydi-benzoylmethane, 2-hydroxy- 4-methoxybenzophenone, octyldimethyl-paminobenzoic acid, digalloyltrioleate, 2,2-dihydroxy4-ethoxy-benzophenone, ethyl-4-[bis(hydroxypropyl)]-aminobenzoate, 2-ethyl-hexyl-2-cyano-3,3diphenylacrylate, 2ethylhexylsalicylate, glyceryl-aminobenzoate, 3,3,5-tfimethyl-cyclohexylsalicylate, methylanthranilate, p-dimethylaminoben-zoic acid or amino-benzoate, 2-ethylhexyl-p-dimethylaminoben-zoate, 2-phenyl-benzimidazole-5-sulfonic acid, 2-(p-dimethyl aminophenyl)-5-sulfonicbenzoxazoic acid and mixtures of these compounds, are particularly useful. Preferred sunscreens useful in the compositions of the present invention are 2-ethylhexyl-p-methoxycinnamate, butyl methoxy-dibenzoylmethane, 2-hydroxy-4-methoxybenzophenone, octyl dimethyl- p-aminobenzoic acid and mixtures thereof.

A safe and effective amount of sunscreen may be used in the compositions of the present invention. The sunscreening agent must be compatible with the anti-wrinkle agent. Generally the composition may comprise from about 1% to about 20%, preferably from about 2% to about 10%, of a sunscreening agent. Exact amounts will vary depending upon the sunscreen chosen and the desired Sun Protection Factor (SPF).

Also particularly useful in the present invention are sunscreens such as those disclosed in Sabatelli, U.S. patent application Ser. No. 054,085 (filed Jun. 2, 1987) and Sabatelli et al., U.S. patent application Ser. No 054,046 (filed Jun. 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. Preferred members of this class of sunscreening agents are 4-N,N-(2-ethylhexyl)methylaminobenzoic acid ester of 2,4-dihydroxy-benzophenone; N,N-di-( 2-ethylhexyl)-4-aminobenzoic acid ester with 4-hydroxydibenzoylmethane; 4-N,N-( 2 ethylhexyl)methylaminobenzoic acid ester with 4-hydroxydibenzoylmethane; 4-N,N-(2-ethylhexyl)methyl-aminobenzoic acid ester of 2-hydroxy-4-(2-hydroxyethoxy)benzophenone; 4-N,N-(2-ethylhexyl)-methylaminobenzoic acid ester of 4-(2-hydroxy-ethoxy)dibenzoylmethane; N,N-di-(2-ethylhexyl)- 4-aminobenzoic acid ester of 2-hydroxy-4-(2-hydroxyethoxy)benzophenone; and N,N-di-(2-ethylhexyl)-4aminobenzoic acid ester of 4-( 2-hydroxyethoxy)-dibenzoylmethane and mixtures thereof.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred wrinkle and atrophy regulating composition of the present invention, an anti-inflammatory agent is included as an active agent along with the anti-wrinkle agent. The inclusion of an anti-inflammatory agent enhances the wrinkle regulating benefits of the compositions. The anti-inflammatory agent protects strongly in the UVA radiation range (though it also provides some UVB protection as well) thereby preventing further wrinkle formation caused by UV radiation, while the anti-wrinkle agent regulates existing wrinkles and skin atrophy. Thus the combination provides broad protection. The topical use of anti-inflammatory agents reduces photo-aging of the skin result ing from chronic exposure to UV radiation. (See U.S. Pat. No. 4,847,071, Bissett, Bush, and Chatterjee, issued Jul. 11, 1989, incorporated herein by reference; and U.S. Pat. No.

4,847,069, Bissett and Chatterjee, issued Jul. 11, 1989, incorporated herein by reference.) A safe and effective amount of an anti-inflammatory agent may be added to the compositions of the present invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednyli dene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and thereof may be used. The preferred steroidal anti-inflammatory for use in the present invention is hydrocortisone. A second class of anti-inflammatory agents which is useful in the compositions of the present invention includes the non steroidal anti-inflammatory agents. The variety of compounds encompassed by this group mixtures are well-known to those skilled in the art. For detailed disclosure of the chemical structure, synthesis, side effects, etc., of non-steroidal anti-inflammatory agents, reference may be had to standard texts, including Anti inflammatory and Anti-Rheumatic Drugs, K. D. Rainsford, Vol. I–III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition of the present invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a fiufenamic acid derivative, is particularly useful for topical application. Of the nonsteroidal anti-inflammatory agents, ibuprofen, napfox en, fiufenamic acid, mefenamic acid, meclofenamic acid, piroxicam and felbinac are preferred; ibuprofen, naproxen, and fiufenamic acid are most preferred.

Another class of anti-inflammatory agents which are useful in the present invention are the anti-inflammatory agents dis closed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di- tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(–)-3'-methyl-5'-hexynoyl)- 2,6-di-t-butyl phenol; 4-((R)-(+)-3'-methyl-5'-hexynoyl)-2,6-di-t-butylphenol; and 4-(3', 3'-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)2-butyl ester, (S)-naproxen-(R)-2-butylester, (S)-naproxol-(R)2-methyl butyrate, (S)-naproxol-(S)-2-methyl butyrate, diastero roetic mixtures of (S)-naproxen-(S)-2-butyl ester and (S)naprox en- (R)-2-butyl ester, and diasteromeric mixtures of (S)-naprox ol- (R)-2-methyl butyrate and (S)-naproxol-(S)-2-methyl butyrate are useful in the present invention.

Finally, so-called "natural" anti-inflammatory agents are useful in the present invention. For example, candelilla wax, alpha bisabolol, aloe vera, Manjistha (extracted from plants in the genus Rubia, particularly *Rubia cordifolia*), and Guggal (extracted from plants in the genus Commiphora, particularly *Commiphora mukul*), may be used.

Another preferred composition of the present invention comprises the anti-wrinkle agent, a sunscreen, and an anti-inflammatory agent together for wrinkle and/or atrophy regulation in the amounts disclosed for each individually hereinabove.

C. Anti-Oxidants/Radical Scavengers

In a preferred wrinkle and atrophy regulating composition of the present invention, an anti-oxidant/radical scavenger is included as an active agent along with the anti-wrinkle agent. The inclusion of an anti-oxidant/radical scavenger increases the wrinkle regulating benefits of the composition.

A safe and effective amount of an anti-oxidant/radical scavenger may be added to the compositions of the present invention, preferably from about 0.1% to about 10%, more preferably from about 1% to about 5%, of the composition. Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2carboxylic acid (commercially available under the tradename TroloxR), gallic acid and its alkyl esters, especially propyl gallate, uric acid and its salts and alkyl esters, sorbic acid and its salts, the ascorbyl esters of fatty acids, amines (e.g., N,Ndiethylhydroxylamine, aminoguanidine), sulfhydryl compounds (e.g., glutathione), and dihydroxy fumaric acid and its salts may be used.

In a preferred wrinkle regulating composition of the present invention, compositions comprise one, any two, or all three of a sunscreening agent, anti-inflammatory agent, and/or an antioxidant/radical scavenging agent included as actives along with the anti-wrinkle agent. The inclusion of two or all three of these agents with the anti-wrinkle agent increases the wrinkle regulating benefits of the composition.

D. Chelators

In a preferred wrinkle and atrophy regulating composition of the present invention, a chelating agent is included as an active agent along with the anti-wrinkle agent. As used herein, "chelating agent" means an active agent capable of removing a metal ion from a system by forming a complex so that the metal ion cannot readily participate in or catalyze chemical reactions. The inclusion of a chelating agent increases the wrinkle regulating benefits of the composition.

A safe and effective amount of a chelating agent may be added to the compositions of the present invention, preferably from about 0.1% to about 10%, more preferably from about 1% to about 5%, of the composition. Chelators useful in compositions of the present invention are disclosed in U.S. patent application Ser. No. 251,910, Bissett, Bush & Chatterjee, filed Oct. 4, 1988, incorporated herein by reference. Preferred chelators useful in compositions of the present invention are furildioxime and derivatives thereof, more preferably amphi-2-furildioxime.

In a preferred wrinkle and atrophy regulating composition of the present invention, compositions comprise one, any two, any three, or all four of a sunscreening agent, anti-inflammatory agent, anti-oxidant/radical scavenging agent, and/or chelating agent included as actives along with the anti-wrinkle agent. The inclusion of two, three, or all four of these agents with the anti-wrinkle agent increases the wrinkle regulating benefits of the composition.

E. Retinoids

In a preferred wrinkle and atrophy regulating composition of the present invention, a retinoid, preferably retinoic acid, is included as an active agent along with the anti-wrinkle agent. The inclusion of a retinoid increases the wrinkle regulating benefits of the composition. A safe and effective amount of a retinoid may be added to the compositions of the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

F. Benzofuran Derivatives

In a preferred wrinkle and atrophy regulating composition of the present invention, a benzofuran derivative, preferably amiodarone, is included as an active agent along with the anti-wrinkle agent. The inclusion of a benzofuran derivative increases the wrinkle regulating benefits of the composition.

A safe and effective amount of a benzofuran derivative may be added to the compositions of the present invention, preferably from about 0.01% to about 20%, more preferably from about 0.1% to about 10%, of the composition. Benzofuran derivatives useful in the present invention are disclosed in U.S. Pat. No. 5,118,707, Chatterjee and Kapoor, issued Jun. 2, 1992, incorporated herein by reference.

In a preferred wrinkle regulating composition of the present invention, compositions comprise one, any two, any three, any four, any five, and or all six of a sunscreening agent, anti-inflammatory agent, anti-oxidant/radical scavenging agent, chelating agent, retinoid, and/or benzofuran derivative included as actives along with the anti-wrinkle agent. The inclusion of two, three, four, five or all six of these agents with the anti-wrinkle agent increases the wrinkle regulating benefits of the composition.

G. N-acetyl-L-cysteine

In a preferred anti-wrinkle composition of the present invention, N-acetyl-L-cysteine (NAC), is included as an active agent along with the anti-wrinkle agent. The inclusion of NAC increases the wrinkle regulating benefits of the composition.

A safe and effective amount of NAC may be added to the compositions of the present invention, preferably from about 0.1% to about 50%, more preferably 0.1% to about 20%, more preferably still from about 2% to about 5%, of the composition.

In a preferred anti-wrinkle composition of the present invention compositions comprise one, any two, any three, any four, any five, any six, and/or all seven of a sunscreening agent, an anti-inflammatory agent, an antioxidant/radical scavenging agent, a chelating agent, a retinoid, a benzofuran derivative, and/or NAC included as actives along with the anti-wrinkle agent. The inclusion of two, three, four, five, six or all seven of these agents with the anti-wrinkle agent increases the wrinkle regulating benefits of the composition.

Methods for Regulating Wrinkles in Mammalian Skin

The present invention further relates to a method for regulating wrinkles in mammalian skin. Such a method comprises treating the skin with a safe and effective amount of the anti-wrinkle agent. The amount of anti-wrinkle agent and frequency of treatment will vary widely depending upon the level of wrinkling already in existence in the subject, the rate of further wrinkle formation, and the level of regulation desired.

A preferred method of treating the skin is via cutaneous injection of a safe and effective amount of the anti-wrinkle agent to regulate wrinkles in mammalian skin. The carrier for injectable administration of the anti-wrinkle agent would preferably comprise water or a saline solution. The amount of anti-wrinkle agent and the frequency of cutaneous injection can vary widely, depending on personal needs. As an example of treatment by cutaneous injection, it is suggested that a composition suitable for cutaneous injection comprising the anti-wrinkle agent be cutaneously injected from once per day to once every six months, preferably from three times per week to once per month, more preferably from once per week to twice per month. The composition for cutaneous injection will contain from about 0.0001% to about 10%, preferably from about 0.001% to about 5%, more preferably from about 0.01% to about 1% of the anti-wrinkle agent. The period of injections would be over a period of from about one month to about ten years, preferably from about three months to about two years, more preferably from about six months to about one year, thereby resulting in regulation of wrinkles in mammalian skin.

A more preferred method of treating the skin is via topical application of a safe and effective amount of the anti-wrinkle agent to regulate wrinkles in mammalian skin. The amount of anti-wrinkle agent and frequency of topical application to the skin can vary widely, depending upon personal needs, but it is suggested as an example that topical application range from about once per week to about 10 times daily, preferably from about twice per week to about 4 times daily, more preferably from about 3 times a week to about twice daily, most preferably about once per day. The composition for topical application will comprise from about 0.001% to about 20%, preferably from about 0.01% to about 10%, more preferably from about 0.1% to about 5% of the anti-wrinkle agent. The period of topical application would preferably be over a period of from about one month to about ten years, more preferably from about three months to about two years, more preferably still from about six months to about one year, thereby resulting in regulation of wrinkles in mammalian skin. A preferred method of the present invention for regulating wrinkles in mammalian skin involves applying both a safe and effective amount of the anti-wrinkle agent and a safe and effective amount of one or more of a sunscreening agent, an antiinflammatory agent, an anti-oxidant/radical scavenging agent, a chelating agent, a retinoid and/or a benzofuran derivative to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.02 mg to about 1.0 mg per cm2 skin. The amount of anti-inflammatory agent applied is generally from about 0.005 mg to about 0.5 mg, preferably from about 0.01 mg to about 0.1 mg per cm2 skin. The amount of anti-oxidant/radical scavenging agent generally applied is from about 0.001 mg to about 1.0 mg, preferably from about 0.05 mg to about 0.5 mg per cm2 skin. The amount of chelating agent generally applied is from about 0.001 mg to about 1.0 mg, preferably from about 0.01 mg to about 0.5 mg, more preferably from about 0.05 mg to about 0.1 mg per cm2 skin. The amount of retinoid applied is generally from about 0.00001 mg to about 0.02 mg per cm2 skin, preferably from about 0.001 mg to about 0.01 mg per cm2 skin. The amount of benzofuran derivative applied is generally from about 0.001 mg to about 1.0 mg/cm2 skin per application, preferably from about 0.01 to about 0.5 mg/cm2 skin per application. The amount of anti-wrinkle agent applied is generally from about 0.001 mg to about 2 mg per cm2 skin per application, preferably from about 0.01 mg to about 1 mg per cm2 skin per application.

The following examples further describe and demonstrate certain preferred embodiments within the scope of the present invention. These preparations may be formulated over a range of pH's, preferably pH 3–10. The examples are given solely for the purpose of illustration, and are not to be construed as limitations of the present invention since many variations thereof are possible without departing from its spirit and scope.

EXAMPLES 4–11

An oil-in-water emulsion is prepared by combining the following components utilizing conventional mixing techniques.

This composition is useful for topical application to regulate skin wrinkles. An amount of the composition sufficient to deposit about 0.01 mg/cm$^2$ of the anti-wrinkle agent to the skin is used. The composition is applied once per day for the subject's lifetime.

EXAMPLES 12–19

A clear gel is prepared by combining the following components utilizing conventional mixing techniques.

| Component | Example No. | | | | | | | |
|---|---|---|---|---|---|---|---|---|
| | 4 | 5 | 6 | 7 | 8 | 9 | 10 | 11 |
| H—Arg—Lys—Arg—OH | 0.1 | — | — | — | — | — | — | — |
| H—Arg—Gly—Arg—Lys—OH (SEQ ID NO:1) | — | 0.1 | — | — | — | — | — | — |
| H—Lys—Arg—Ser—NH$_2$ | — | — | 0.1 | — | — | — | — | — |
| H$_3$C—C(O)—Arg—Lys—Arg—NH$_2$ | — | — | — | 0.1 | — | — | — | — |
| Arg—Ser—Arg—Lys (SEQ ID NO:3) (L-form, unblocked and unprotected) | — | — | — | — | 0.1 | — | — | — |
| n-C$_{20}$H$_{41}$—Arg—Ser—Arg—Lys—n-C$_{18}$H$_{39}$ (L-form, unblocked and unprotected) | — | — | — | — | — | 0.1 | — | — |
| Tos—Arg—Ser—Arg—Lys—Tyr—B$_2$l (serine in D-form) | — | — | — | — | — | — | 0.1 | — |
| Tyr—Arg—Ser—Arg—Lys—Tyr (SEQ ID NO:4) (L-form, unblocked and unprotected) | — | — | — | — | — | — | — | 0.1 |
| Glycerin | 3 | 3 | 3 | 3 | 3 | 3 | 3 | 3 |
| Methyl paraben | 0.2 | 0.2 | 0.2 | 0.2 | 0.2 | 0.2 | 0.2 | 0.2 |
| Steareth 20 (Brij 78R) | 1 | 1 | 1 | 1 | 1 | 1 | 1 | 1 |
| Glyceryl monostearate and PEG 100 (Arlacel 165R) | 0.5 | 0.5 | 0.5 | 0.5 | 0.5 | 0.5 | 0.5 | 0.5 |
| Carbopol 940 (B. F. Goodrich, Cleveland, OH) | 0.2 | 0.2 | 0.2 | 0.2 | 0.2 | 0.2 | 0.2 | 0.2 |
| 99% triethanolamine | 0.2 | 0.2 | 0.2 | 0.2 | 0.2 | 0.2 | 0.2 | 0.2 |
| Cetyl alcohol | 1 | 1 | 1 | 1 | 1 | 1 | 1 | 1 |
| Stearyl alcohol | 1 | 1 | 1 | 1 | 1 | 1 | 1 | 1 |
| Propyl paraben | 0.1 | 0.1 | 0.1 | 0.1 | 0.1 | 0.1 | 0.1 | 0.1 |
| Disiopropyldimerate | 2 | 2 | 2 | 2 | 2 | 2 | 2 | 2 |
| C$_{12}$–C$_{15}$ alcohol benzoate | 6 | 6 | 6 | 6 | 6 | 6 | 6 | 6 |
| Imidazolidinol urea | 0.3 | 0.3 | 0.3 | 0.3 | 0.3 | 0.3 | 0.3 | 0.3 |
| Deionized water | Balance to 100% | | | | | | | |

|  | Example No. | | | | | | | |
|---|---|---|---|---|---|---|---|---|
| Component | 12 | 13 | 14 | 15 | 16 | 17 | 18 | 19 |
| H—Arg—Lys—Arg—OH | 0.5 | — | — | — | — | — | — | — |
| H—Arg—Gly—Arg—Lys—OH (SEQ ID NO:1) | — | 0.5 | — | — | — | — | — | — |
| H—Lys—Arg—Ser—NH$_2$ | — | — | 0.5 | — | — | — | — | — |
| H$_3$C—C(O)—Arg—Lys—Arg—NH$_2$ | — | — | — | 0.5 | — | — | — | — |
| Arg—Ser—Arg—Lys (SEQ ID NO:3) (L-form, unblocked and unprotected) | — | — | — | — | 0.5 | — | — | — |
| n-C$_{20}$H$_{41}$—Arg—Ser—Arg—Lys—n-C$_{18}$H$_{39}$ (L-form, unblocked and unprotected) | — | — | — | — | — | 0.5 | — | — |
| Tos—Arg—Ser—Arg—Lys—Tyr—B$_2$l (serine in D-form) | — | — | — | — | — | — | 0.5 | — |
| Tyr—Arg—Ser—Arg—Lys—Tyr (SEQ ID NO:4) (L-form, unblocked and unprotected) | — | — | — | — | — | — | — | 0.5 |
| Carbopol 980 (B. F. Goodrich, Cleveland, OH) | 0.5 | 0.5 | 0.5 | 0.5 | 0.5 | 0.5 | 0.5 | 0.5 |
| Disodium EDTA | 0.02 | 0.02 | 0.02 | 0.02 | 0.02 | 0.02 | 0.02 | 0.02 |
| 99% triethanolamine | 0.5 | 0.5 | 0.5 | 0.5 | 0.5 | 0.5 | 0.5 | 0.5 |
| Propylene glycol | 3 | 3 | 3 | 3 | 3 | 3 | 3 | 3 |
| Methyl paraben | 0.2 | 0.2 | 0.2 | 0.2 | 0.2 | 0.2 | 0.2 | 0.2 |
| Deionized water | Balance to 100% | | | | | | | |

This composition is useful for topical application to regulate skin wrinkles. An amount of the composition sufficient to deposit about 0.01 mg/cm$^2$ of anti-wrinkle agent to the skin is used. The composition is applied three times per day over a six-month period.

EXAMPLES 20–27

An oil-in-water polymer emulsion is prepared by combining the following components utilizing conventional mixing techniques.

This composition is useful for topical application to regulate skin wrinkles. An amount of the composition sufficient to deposit 0.1 mg/cm2 anti-wrinkle agent to the skin is used. The composition is applied once per week over a one-year period.

EXAMPLES 28–35

An oil-in-water microemulsion is prepared by combining the following components utilizing conventional mixing techniques.

|  | Example No. | | | | | | | |
|---|---|---|---|---|---|---|---|---|
| Component | 20 | 21 | 22 | 23 | 24 | 25 | 26 | 27 |
| H—Arg—Lys—Arg—OH | 0.75 | — | — | — | — | — | — | — |
| H—Arg—Gly—Arg—Lys—OH (SEQ ID NO: 1) | — | 0.75 | — | — | — | — | — | — |
| H—Lys—Arg—Ser—NH$_2$ | — | — | 0.75 | — | — | — | — | — |
| H$_3$C—C(O)—Arg—Lys—Arg—NH$_2$ | — | — | — | 0.75 | — | — | — | — |
| Arg—Ser—Arg—Lys (SEQ ID NO:3) (L—form, unblocked and unprotected) | — | — | — | — | 0.75 | — | — | — |
| n-C$_{20}$H$_{41}$—Arg—Ser—Arg—Lys—n-C$_{18}$H$_{39}$ (L-form, unblocked and unprotected) | — | — | — | — | — | 0.75 | — | — |
| Tos—Arg—Ser—Arg—Lys—Tyr—B$_2$l (serine in D-form) | — | — | — | — | — | — | 0.75 | — |
| Tyr—Arg—Ser—Arg—Lys—Tyr (SEQ ID NO:4) (L-form, unblocked and unprotected) | — | — | — | — | — | — | — | 0.75 |
| Carbopol 954 (B. F. Goodrich, Cleveland, OH) | 0.2 | 0.2 | 0.2 | 0.2 | 0.2 | 0.2 | 0.2 | 0.2 |
| Pemulen TR-2 (B. F. Goodrich, Cleveland, OH) | 0.15 | 0.15 | 0.15 | 0.15 | 0.15 | 0.15 | 0.15 | 0.15 |
| Glycerin | 3 | 3 | 3 | 3 | 3 | 3 | 3 | 3 |
| 99% triethanolamine | 0.35 | 0.35 | 0.35 | 0.35 | 0.35 | 0.35 | 0.35 | 0.35 |
| Cetyl palmitate | 2 | 2 | 2 | 2 | 2 | 2 | 2 | 2 |
| Stearoxy trimethyl silane and stearyl alcohol | 1 | 1 | 1 | 1 | 1 | 1 | 1 | 1 |
| Squalane | 6 | 6 | 6 | 6 | 6 | 6 | 6 | 6 |
| Propyl paraben | 0.1 | 0.1 | 0.1 | 0.1 | 0.1 | 0.1 | 0.1 | 0.1 |
| Methyl paraben | 0.2 | 0.2 | 0.2 | 0.2 | 0.2 | 0.2 | 0.2 | 0.2 |
| Imidazolidinol urea | 0.3 | 0.3 | 0.3 | 0.3 | 0.3 | 0.3 | 0.3 | 0.3 |
| Deionized water | Balance to 100% | | | | | | | |

| Component | Example No. | | | | | | | |
|---|---|---|---|---|---|---|---|---|
| | 28 | 29 | 30 | 31 | 32 | 33 | 34 | 35 |
| H—Arg—Lys—Arg—OH | 1 | — | — | — | — | — | — | — |
| H—Arg—Gly—Arg—Lys—OH (SEQ ID NO: 1) | — | 1 | — | — | — | — | — | — |
| H—Lys—Arg—Ser—$NH_2$ | — | — | 1 | — | — | — | — | — |
| $H_3C$—C(O)—Arg—Lys—Arg—$NH_2$ | — | — | — | 1 | — | — | — | — |
| Arg—Ser—Arg—Lys (SEQ ID NO:3) (L-form, unblocked and unprotected) | — | — | — | — | 1 | — | — | — |
| n-$C_{20}H_{41}$—Arg—Ser—Arg—Lys—n-$C_{18}H_{39}$ (L-form, unblocked and unprotected) | — | — | — | — | — | 1 | — | — |
| Tos—Arg—Ser—Arg—Lys—Tyr—$B_2l$ (serine in D-form) | — | — | — | — | — | — | 1 | — |
| Tyr—Arg—Ser—Arg—Lys—Tyr (SEQ ID NO:4) (L-form, unblocked and unprotected) | — | — | — | — | — | — | — | 1 |
| PEG4 sorbitan monolaurate | 22.5 | 22.5 | 22.5 | 22.5 | 22.5 | 22.5 | 22.5 | 22.5 |
| PEG5 sorbitan monooleate | 2.5 | 2.5 | 2.5 | 2.5 | 2.5 | 2.5 | 2.5 | 2.5 |
| Cetearyl octanoate | 25 | 25 | 25 | 25 | 25 | 25 | 25 | 25 |
| DMDM hydantoin and 3-iodo-2-propynylbutyl carbamate (glydant plus) | 0.2 | 0.2 | 0.2 | 0.2 | 0.2 | 0.2 | 0.2 | 0.2 |
| Deionized water | Balance to 100% | | | | | | | |

This composition is useful for topical application to regulate skin wrinkles. An amount of the composition sufficient to deposit 0.4 mg/cm2 anti-wrinkle agent to the skin is used. The composition is applied three times per week over a five-year period.

Compositions of the present invention may also be used in conjunction with various surgical procedures for wrinkle removal such as chemical peel, dermabrasion, laser abrasion and collagen injections.

The foregoing additionally represents an improvement for the cosmetic treatment of wrinkles in mammalian skin.

While particular embodiments of the subject invention have been described, it will be obvious to those skilled in the art that various changes and modifications of the subject invention can be made without departing form the spirit and scope of the invention. It is intended to cover, in the appended claims, all such modifications that are within the scope of the invention.

---

What is claimed is:

1. A topical composition comprising:

a) a peptide useful for cosmetic treatment of mammalian skin wrinkles having the amino acid sequence $$Q^a\text{-}(Xaa)_n\text{-}Q^c$$

wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl;

$Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (allcyl)(arylalkyl)amino, (aryl)(arylaikyl)amino, and amino;

n is from 3 to 6;

Xaa is independently any amino acid; wherein at least three of the Xaa are independently selected from the group consisting of arginine and lysine; and b) a pharmaceutically-acceptable carrier or cosmetically-acceptable carrier, wherein the carrier is a topical carrier comprising an emollient.

2. The composition of claim 1 which comprises from about 0.001% to about 20% of the peptide, wherein Xaa is independently selected from the group consisting of Ala, Arg, Asn, Asp, Cys, Gln, Glu, Gly, His, Ile, Leu, Lys, Met, Phe, Pro, Ser, Thr, Trp, Tyr and Val.

3. The composition of claim 2 wherein at least two of Xaa are Arg and at least one of Xaa is Lys.

4. The composition of claim 3 wherein $Q^a$ is hydrogen and $Q^c$ is hydroxy.

5. The composition of claim 4 wherein the peptide is H-Arg-Ser-Arg-Lys-OH (SEQ ID NO:3).

6. The composition of claim 4 wherein n is 3.

7. The composition of claim 6 wherein the peptide is H-Arg-Lys-Arg-OH.

8. The composition of claim 3 wherein the peptide is $H_3C$-C(O)-Arg-Lys-Arg-$NH_2$.

9. The composition of claim 4 wherein n is 4.

10. The composition of claim 9 wherein the peptide is H-Arg-Gly-Arg-Lys-OH (SEQ ID NO: 1).

11. The composition of claim 3 wherein $Q^a$ is hydrogen and $Q^c$ is $NH_2$.

12. The composition of claim 11 wherein the peptide is H-Lys-Arg-Ser-Arg-$NH_2$.

13. The composition of claim 1 which additionally comprises a safe and effective amount of an active selected from the group consisting of a sunscreening agent, an anti-inflammatory agent, an anti-oxidant/radical scavenging agent, a chelator, a retinoid, and N-acetyl cysteine.

14. The composition of claim 1 which additionally comprises a safe and effective amount of a sunscreening agent and a safe and effective amount of an anti-inflammatory agent.

15. A method for the cosmetic treatment of mammalian skin wrinkles comprising topically applying to mammalian skin in need of such treatment a composition comprising:

a) peptide useful for the cosmetic treatment of mammalian skin wrinkles having the areinc acid sequence $Q^a$-$(Xaa)_n$-$Q^c$ wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl;

$Q^c$ is selected from the group consisting of hydroxy, alkyloxy, aryloxy, arylalkyloxy, allcylamino, dialkylamino, arylamino, diarylamino, (aryl)(alkyl)amino, arylalkylamino, diarylalkylamino, (alkyl)(arylalkyl)amino, (aryl)(arylalkyl)amino, and amino;

n is from 3 to 6;

Xaa is independently any areinc acid; wherein at least three of the Xaa are independently selected from the group consisting of arginine and lysine; and b) a pharmaceutically-acceptable carrier or cosmetically-acceptable carrier wherein the carrier is a topical carrier comprising an emollient.

16. The method of claim 15 wherein at least two of Xaa are Arg and at least one of Xaa is Lys.

17. The method of claim 16 wherein the peptide is H-Arg-Lys-Arg-OH.

18. The method of claim 16 wherein the peptide is $H_3C$-C(O)-Arg-Lys-Arg-$NH_2$.

19. The method of claim 16 wherein the peptide is H-Arg-Gly-Arg-Lys-OH (SEQ ID NO: 1).

20. The method of claim 16 wherein the peptide is H-Lys-Arg-Ser-Arg-$NH_2$.

21. The method of claim 16 wherein the peptide is H-Arg-Ser-Arg-Lys-OH (SEQ ID NO: 3).

22. A peptide useful for the cosmetic treatment of mammalian skin wrinkJes having the amino acid sequence $Q^a$-Arg-Lys-Arg-$Q^c$, wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino.

23. The peptide of claim 22 wherein $Q^a$ is hydrogen and $Q^c$ is hydroxy.

24. The peptide of claim 22 wherein $Q^a$ is $H_3C$—C(O)— and $Q^c$ is amino.

25. A peptide useful for the cossmetic treatment of mammalian skin wrinkles having the amino acid sequence $Q^a$-Arg-Gly-Arg-Lys-$Q^c$, wherein $Q^a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, alkylamino, dialkylamino, arylamino, diarylamino, (aryl)(alkyl)amino, arylalkylamino, diarylalkylamino, (alkyl)(arylalkyl)amino, (aryl)(arylalkyl)amino, and amino.

26. The peptide of claim 25 wherein $Q^a$ is hydrogen and $Q^c$ is hydroxy (SEQ ID NO: 1).

27. A peptide useful for the cosmetic treatment of mammalian skin wrinkles having the amino acid sequence $Q^a$-Lys-Arg-Ser-Arg-$Q^c$, wherein $Q_a$ is selected from the group consisting of hydrogen, alkyl, aryl, arylalkyl, alkyloyl, aryloyl, arylalkyloyl, alkyloxoyl, aryloxoyl and arylalkyloxoyl; and $Q^c$ is selected from the group consisting of hydroxy, alkyloxy, aryloxy, arylalkyloxy, allcylamino, dialkylamino, arylamino, diarylamino, (aryl)(alkyl)amino, arylalkylamino, diarylalkylamino, (alkyl)(arylalkyl)amino, (aryl)(arylalkyl)amino, and amino.

28. The peptide of claim 27 wherein $Q^a$ is hydrogen and $Q^c$ is -$NH_2$.

29. A topical composition comprising:

a) a safe and effective amount of a peptide useful for the cosmetic treatment of mammalian skin wrinkles having the amino acid sequence $Q^a$-$(Xaa)n$ Arg Ser Arg Lys $(Xaa)n$-$Q^c$ wherein each n is independently an integer selected from the group consisting of 0, 1, 2 and 3, each Xaa is independently any amino acid, each amino acid is protected or unprotected, $Q^a$ is selected from the group consisting of hydrogen and an amino-terminus blocking group, and $Q^c$ is selected from the group consisting of hydrogen and a carboxy-terminus blocking group; and b) a safe and effective mount of a topical carrier comprising an emollient.

30. A method for the cosmetic treatment of mammalian skin wrinkles in mammalian skin comprising treating the skin with a safe and effective amount of the composition of claim 29.

* * * * *

UNITED STATES PATENT AND TRADEMARK OFFICE
CERTIFICATE OF CORRECTION

PATENT NO. : 5,492,894
DATED : February 20, 1996
INVENTOR(S) : Bascom et al.

It is certified that error appears in the above-identified patent and that said Letters Patent is hereby corrected as shown below:

Column 5, line 7 "$Q_a$" should read --$Q^a$--.
Column 5, line 11 "$Q_a$" should read --$Q^a$--.
Column 5, line 18 "$Q_a$" should read --$Q^a$--.
Column 6, line 50, "tfityl" should read --trityl--.
Column 6, line 51, "sefine" should read --serine--.
Column 7, line 62, "ceil" should read --cell--.
Column 15, line 5, "Sagafin" should read --Sagarin--.
Column 17, line 14, "bentonitc" should read -bentonite-.
Column 18, line 21, "an-", should read -art-".
Column 43, line 64, "(allcyl)" should read -(alkyl)-.
Column 45, line 33, "allcylamino" should read -alkylamino-.
Column 45, line 38, "areinc" should read -amino-.
Column 45, line 58, "wrinkJes" should read -wrinkles-.
Column 46, line 26, "$Q_a$" should read -$Q^a$-.
Column 46, line 30, "allcylamino" should read -alkylamino-.

Signed and Sealed this

Twenty-first Day of April, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:1:

Arg  Gly  Arg  Lys
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:2:

Lys  Arg  Ser  Arg
1

( 2 ) INFORMATION FOR SEQ ID NO:3:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:3:

Arg Ser Arg Lys
1

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Tyr Arg Ser Arg Lys Tyr
1               5

( 2 ) INFORMATION FOR SEQ ID NO:5:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Tyr Arg Ser Arg Lys
1               5

( 2 ) INFORMATION FOR SEQ ID NO:6:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

Arg Ser Arg Lys Tyr
1               5

( 2 ) INFORMATION FOR SEQ ID NO:7:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

Thr Tyr Arg Ser Arg Lys Tyr Ser
1               5

( 2 ) INFORMATION FOR SEQ ID NO:8:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

Ser Tyr Arg Ser Arg Lys Tyr Thr
1               5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Ser Tyr Arg Ser Arg Lys Tyr Ser
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Thr Tyr Arg Ser Arg Lys Tyr Thr
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Arg Ser Arg Lys Tyr Thr
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Thr Tyr Arg Ser Arg Lys
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Arg Ser Arg Lys Tyr Ser ( 2 ) INFORMATION FOR SEQ ID NO:14:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Ser  Tyr  Arg  Ser  Arg  Lys
1                   5
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Tyr  Arg  Ser  Arg  Lys  Tyr  Thr
1                   5
```

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Thr  Tyr  Arg  Ser  Arg  Lys  Tyr
1                   5
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Tyr  Arg  Ser  Arg  Lys  Tyr  Ser
1                   5
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Ser  Tyr  Arg  Ser  Arg  Lys  Tyr
1                   5
```

( 2 ) INFORMATION FOR SEQ ID NO:19:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

```
Asn Thr Tyr Arg Ser Arg Lys Tyr Ser Ser
1               5                   10
```

( 2 ) INFORMATION FOR SEQ ID NO:20:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:20:

```
Asn Ser Tyr Arg Ser Arg Lys Tyr Thr Ser
1               5                   10
```

( 2 ) INFORMATION FOR SEQ ID NO:21:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:21:

```
Asn Ser Tyr Arg Ser Arg Lys Tyr Ser Ser
1               5                   10
```

( 2 ) INFORMATION FOR SEQ ID NO:22:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:22:

```
Asn Thr Tyr Arg Ser Arg Lys Tyr Thr Ser
1               5                   10
```

( 2 ) INFORMATION FOR SEQ ID NO:23:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:23:

```
Arg Ser Arg Lys Tyr Thr Ser
1               5
```

( 2 ) INFORMATION FOR SEQ ID NO:24:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:24:

```
Asn Thr Tyr Arg Ser Arg Lys
1               5
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Arg Ser Arg Lys Tyr Ser Ser
1               5
```

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Asn Ser Tyr Arg Ser Arg Lys
1               5
```

( 2 ) INFORMATION FOR SEQ ID NO:27:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Tyr Arg Ser Arg Lys Tyr Thr Ser
1               5
```

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
Asn Thr Tyr Arg Ser Arg Lys Tyr
1               5
```

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
Tyr Arg Ser Arg Lys Tyr Ser Ser
```

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:30:

```
Asn  Ser  Tyr  Arg  Ser  Arg  Lys  Tyr
1                    5
```

(2) INFORMATION FOR SEQ ID NO:31:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:31:

```
Thr  Tyr  Arg  Ser  Arg  Lys  Tyr  Ser  Ser
1                    5
```

(2) INFORMATION FOR SEQ ID NO:32:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:32:

```
Asn  Thr  Tyr  Arg  Ser  Arg  Lys  Tyr  Ser
1                    5
```

(2) INFORMATION FOR SEQ ID NO:33:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:33:

```
Ser  Tyr  Arg  Ser  Arg  Lys  Tyr  Thr  Ser
1                    5
```

(2) INFORMATION FOR SEQ ID NO:34:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:34:

```
Asn  Ser  Tyr  Arg  Ser  Arg  Lys  Tyr  Thr
1                    5
```

(2) INFORMATION FOR SEQ ID NO:35:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:35:

Ser Tyr Arg Ser Arg Lys Tyr Ser Ser
1               5

( 2 ) INFORMATION FOR SEQ ID NO:36:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:

Asn Ser Tyr Arg Ser Arg Lys Tyr Ser
1               5

( 2 ) INFORMATION FOR SEQ ID NO:37:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:

Thr Tyr Arg Ser Arg Lys Tyr Thr Ser
1               5

( 2 ) INFORMATION FOR SEQ ID NO:38:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:38:

Asn Thr Tyr Arg Ser Arg Lys Tyr Thr
1               5